United States Patent [19]
Snowden et al.

[11] Patent Number: 5,952,292
[45] Date of Patent: Sep. 14, 1999

US005952292A

[54] UTILIZATION OF 3-METHYL-2-OXO-ETHYL-PENTANOATE AS A PERFUMING INGREDIENT

[75] Inventors: Roger L. Snowden, Viry, France; Hervé Pamingle, Versoix; Christian Vial, Geneva, both of Switzerland

[73] Assignee: Firmenich S.A., Geneve, Switzerland

[21] Appl. No.: 09/204,966

[22] Filed: Dec. 3, 1998

[30] Foreign Application Priority Data

Dec. 8, 1997 [CH] Switzerland .............................. 2825/97

[51] Int. Cl.⁶ ................................. A61K 7/46; A61K 7/00
[52] U.S. Cl. .................................. 512/25; 512/1; 512/26; 512/27; 424/401
[58] Field of Search ..................... 512/1, 25, 26, 512/27; 424/401

[56] References Cited

FOREIGN PATENT DOCUMENTS

WO 96/10927  4/1996  WIPO.

OTHER PUBLICATIONS

R. Kozlowski et al., "Lower Aliphatic 2–Oxoacids and their Ethyl Esters From Ethyl Esters of 2–Hydroxy Acids", Organic Preparations and Procedures Inc. 21(1), 75–82 (1989).

Y. Akiyama et al., "Studies on Conjugated Nitriles. IV.", Chem. Pharm. Bull. 32 (5) 1800–1807 (1984).

Y. Akiyama et al., "Reaction of Organocadmium Reagents with Ethyl Cyanoformate: preparation of α–Keto Ester", Chemistry Letters, pp. 1231–1232, 1983.

P. Yates et al., "Synthesis of piperazine–2,5–diones related to bicyclomycin; 1,4–dibenzyl–3–hydroxy–3–[1–(2–methoxyethyl) ethenyl] piperzaine–2,5–dione, 2. Route via cyclic intermediates". Can. J. Chem. 61970, 1397–1404 (1983).

H.M. Walborsky, "Partial Asymmetric Syntheses of Amino Acids Using Lithium Aldimine Precursors", J. Org. Chem., vol. 39, (5), 604–607, 1974.

L.N. Akimova. "Preparation of Estes of α–Keto Acids by the Actions of Grignard Reagents of Oxalic Esters". Zhurnal Organicheskoi Khimii 5(9) pp. 1569–1571, Sep. 1969.

*Primary Examiner*—Shelley A. Dodson
*Assistant Examiner*—Marina Lamm
*Attorney, Agent, or Firm*—Pennie & Edmonds LLP

[57] ABSTRACT

3-Methyl-2-oxo-ethylpentanoate or an isomer thereof are very useful compounds in the field of perfumery, having an unusual, fruity odor note that can be described as a fresh walnut odor together with a rum type note.

4 Claims, No Drawings

UTILIZATION OF 3-METHYL-2-OXO-ETHYL-PENTANOATE AS A PERFUMING INGREDIENT

BRIEF SUMMARY OF THE INVENTION

The invention belongs to the field of perfumery. It relates more particularly to the use of 3-methyl-2-oxo-ethyl-pentanoate of formula

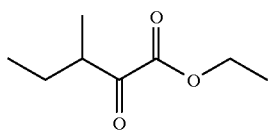

(I)

in the form of an optically active isomer or a mixture of isomers, as a perfuming ingredient.

BACKGROUND OF THE INVENTION

The structure of 3-methyl-2-oxo-ethyl-pentanoate, in racemic form is known. Several references have disclosed it, either mentioning only the molecule, or describing its preparation in detail. In this context, the following references can be cited: R. Kozlowski et al., Org. Prep. Proceed. Int., 21(1), 75–82 (1989); Y. Akiyama et al., Chem. Pharm. Bull. 32(5), 1800–1807 (1984); Y. Akiyama et al., Chem. Lett. 8, 1231–1232 (1983); P. Yates et al., Can. J. Chem. 61(7), 1397–1404 (1983); H. M. Walborsky et al., J. Org. Chem. 39(5), 604–607 (1974); L. N. Akimova et al., Zh Org. Khim. 5(9), 1569–1571 (1969). However none of these references either describes the odor of said ester or suggests its utilization in the field of perfumery.

Moreover, the acids of formula

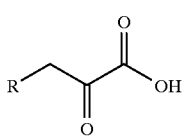

(II)

wherein R can be hydrogen or represents a great variety of alkyl radicals, saturated or unsaturated, linear or branched, and namely 3-methyl-2-oxopentanoic acid, are known to be used in the field of flavors. The international application WO 96/10927 describes the utilization of this group of compounds in a variety of foods, to which they impart an enhanced impact in the mouth. The $C_1$ to $C_4$ alkyl esters of said acids are also mentioned as useful flavoring ingredients in a general manner, without however giving any concrete example of preparation or even of application of these alkyl esters. Once again there is no description of the olfactory characteristics of the esters of this invention.

DETAILED DESCRIPTION OF THE INVENTION

Surprisingly, we have been able to establish that the 3-methyl-2-oxo-ethylpentanoate, or an isomer thereof, are very useful perfuming ingredients, having an unknown and unusual odor, which is a combination of fresh and fruity notes with a walnut type odor character.

The invention is thus related to a method to confer, improve, enhance or modify the odor properties of a perfuming composition or a perfumed product, which method comprises adding 3-methyl-2-oxo-ethylpentanoate, or an isomer thereof, as perfuming ingredients to said composition or product.

More particularly, the esters of the invention present a complex odor note of the walnut type, that can be described as being reminiscent of the odor of a fresh walnut, together with a walnut husk character. This note is surprisingly fruity; moreover, there is also a hazelnut connotation. The characteristic walnut-fresh hazelnut note is accompanied by an odor which is reminiscent of that of rum. In sum, the odor is very natural, excellent and unusual.

The 3-methyl-2-oxo-ethyl-pentanoate brings a new odor note to the perfumer's palette, a fruity, walnut note which is very natural and which was not available until today. This unusual combination of fruity connotation with a very natural walnut-rum odor renders the compound of this invention of great value for use in perfumery.

Moreover, we have been able to evaluate the organoleptic properties of the optically active isomers: while (+)-ethyl-(S)-3-methyl-2-oxopentanoate presents a typical walnut note, accompanied by a walnut-husk, pungent, etheral, slightly fruity odor, (−)-ethyl-(R)-3-methyl-2-oxopentanoate also has a typical walnut note, but its odor is more pungent, more dry, less powerful and does not posses the fruity-apple note.

The compounds of the invention are particularly useful in fine perfumery, namely in perfumes, colognes or after-shave lotions.

It goes without saying that their utilization is not limited to the above-mentioned products, and these compounds can suit any other usual application in perfumery, namely to perfume soaps and shower or bath gels, hygiene or hair care products such as shampoos and also body or ambient air deodorants and cosmetic preparations.

The compounds can also be used in applications such as liquid or solid detergents for textile treatment, fabric softeners, or yet detergent compositions or cleaning products for dishes or varied surfaces, for a domestic as well as an industrial use.

In these applications, they can be used alone as well as mixed with other perfuming ingredients, solvents or additives commonly used in perfumery. The nature and variety of these coingredients do not require a more detailed description here, which would not be exhaustive anyway. In fact, a person skilled in the art, having a general knowledge, is able to choose them according to the nature of the product that has to be perfumed and the olfactory effect sought. These perfuming ingredients belong to varied chemical groups such as alcohols, aldehydes, ketones, esters, acetates, nitriles, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., U.S.A., or more recent versions thereof, or in other similar books.

The proportions in which the compounds according to the invention can be incorporated in the different products mentioned above vary in a broad range of values. These values depend on the nature of the product that has to be perfumed and on the olfactory effect sought, as well as on the nature of the coingredients in a given composition when the compounds of the invention are used in admixture with perfuming coingredients, solvents or additives commonly used in the art.

For instance, concentrations from 0.1 to 10% by weight of these compounds with respect to the weight of the perfuming composition in which they are incorporated, can be used. Much lower concentrations than these can be used when these compounds are directly applied for perfuming some of the consumer products mentioned above.

The invention also relates to a process for the preparation of each of the optically active esters of the invention, starting respectively from the corresponding hydroxyesters, namely (+)-ethyl-(2S, 3S)-2-hydroxy-3-methylpentanoate and (+)-ethyl-(2S, 3R)-2-hydroxy-3-methylpentanoate. Both reactions are carried out in a similar way, adding successively sodium acetate and pyridinium chlorochromate to a solution of (+)-ethyl-(2S, 3S)-2-hydroxy-3-methylpentanoate, respectively (+)-ethyl-(2S, 3R)-2-hydroxy-3-methylpentanoate. These synthesis, as well as the preparation of the hydroxyesters, will be described in more detail in the examples presented further on.

The invention will now be described in greater detail in the following examples, wherein the temperatures are indicated in degrees centigrade and the abbreviations have the usual meaning in the art.

EXAMPLE 1

Preparation of the Optically Active Isomers According to the Invention

1. Synthesis of (+)-ethyl-(S)-3-methyl-2-oxopentanoate

The synthesis was carried out in three steps, according to the following scheme:

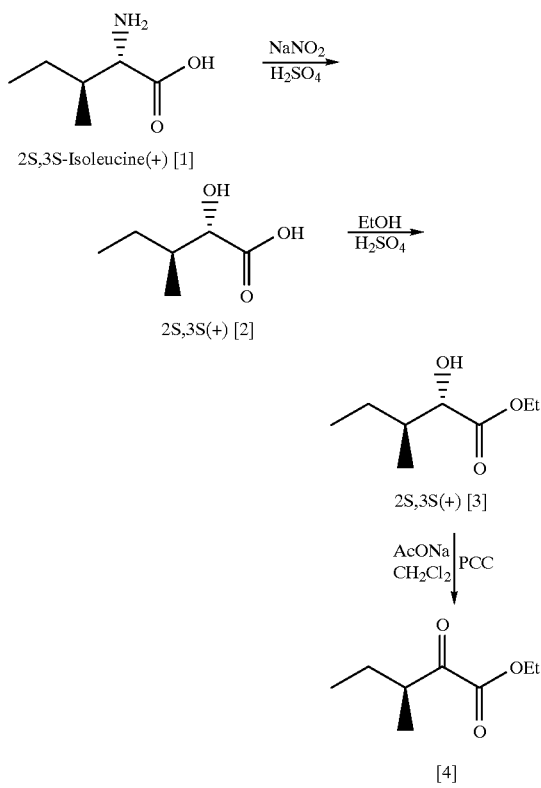

1.1. Synthesis (+)-(2S, 3S)-2-hydroxy-3-methylpentanoic acid [2]

To a solution of L-isoleucine(+) [1] (11.73 g, 89.4 mmol, $[\alpha]^D{}_{20}=+40°$ (5% in 6M HCl)) in 300 ml of 1N aq. $H_2SO_4$ at 2° was slowly added (ca. 12 h) a solution of $NaNO_2$ (19.5 g, 0.28 mol) in 300 ml of demineralised water. After stirring overnight at room temperature, 7.7 g of powdered $NaHCO_3$ were added to bring the pH above 2. The solution was saturated with NaCl and extracted 6 times with ethyl acetate, maintaining the pH between 2 and 3 (1N aq. $H_2SO_4$, pH meter). After drying ($Na_2SO_4$), the organic layer was concentrated and the crude product (10.73 g, 91%) was recrystallised from hexane/ethyl acetate 9/1 at −30° to give pure (+)-(2S, 3S)-2-hydroxy-3-methylpentanoic acid [2].

Analytical data: m.p.=52–54° $[\alpha]^D{}_{20}=+22.4°$ (1.25% in $CHCl_3$) MS: 132($M^+$, 0): m/e: 87(28), 76(100), 69(12), 57(25), 45(23), 29(14) $^1$H-NMR($CDCl_3$): 0.90(t, J=7, 3H); 0.98(d, J=7, 3H); 1.26(m, 1H); 1.41(m, 1H); 1.83(m, 1H ); 4.13(d, $J_1$=4) $^{13}$C-NMR($CDCl_3$): 2q: 11.7, 15.2; 1t: 23.8; 2d: 38.7, 74.7; 1s: 177.9

1.2. Synthesis of (+)-ethyl-(2S, 3S)-2-hydroxy-3-methylpentanoate [3]

To a solution of (+)-hydroxy acid [2] (4.57 g, 34.6 mmol) in 46 ml of absolute ethanol was added 0.3 g of conc. $H_2SO_4$ and the mixture was heated 5 h at 60°. After normal workup and concentration, the compound was distilled (bulb-to-bulb, 110–120°, 18 mbars) to give 4.65 g (yield: 84%) of 95.3% pure (+)-hydroxy ester [3]. A sample was purified by flash chromatography on $SiO_2$ (heptane/ether 65/35). By GC analysis on a chiral column (CHIRASIL-DEX CB, 25 m×0.25 mm, isoth. 90°), the product was found to be enantiomerically pure (contained 2.5% of the 2R, 3S-diastereoisomer.

Analytical data: $[\alpha]^D{}_{20}=+16.7°$ (1.75% in $CHCl_3$) MS: 160($M^+$, 1): m/e: 104(47), 87(95), 76(86), 69(38), 57(32), 45(100), 29(74) $^1$H-NMR($CDCl_3$): 0.90(t, J=7, 3H); 0.99(d, J=7, 3H); 1.30(t, J=7, 3H); 1.19–1.43(m, 2H); 1.81(m, 1H); 2.74(d, J=6, 1H, disappear by add. of $D_2O$); 4.07(dd, $J_1$=4, $J_2$=6, 1H, collapse to d, J=4 by add. of $D_2O$); 4.26(m, 2H) $^{13}$C-NMR($CDCl_3$): 3q: 11.8, 14.2, 15.4; 2t: 23.8, 61.5; 2d: 39.1, 74.6; 1s: 175.0

1.3. Synthesis of (+)-ethyl-(S)-3-methyl-2-oxopentanoate [4]

To a solution of (+)-hydroxy ester [3] (2.0 g, 12.5 mmol) in 20 ml of $CH_2Cl_2$ at room temperature were added successively NaOAc (312 mg, 3.8 mmol) and PCC (pyridinium chlorochromate, 4.04 g, 18.75 mmol). After 24 h at room temperature, the conversion was only 60% and 2.02 g PCC were re-added. The mixture was stirred 96 h at room temperature, rapidly filtered on $SiO_2$, concentrated and purified by flash chromatography on $SiO_2$ to give 1.58 g of ester [4]. At this stage, a GC control on chiral column (CHIRASIL-DEX CB, 25 m×0.25 mm, isoth. 80°) showed a purity of 100% and an ee (enantiomeric excess) of 100%. After bulb-to-bulb distillation (Eb=100°, 16 mbars), 1.51 g (yield: 76.3%) of pure (+)-ester [4] were obtained.

Analytical data: $[\alpha]^D{}_{20}=+38.4°$ (0.7% in $CHCl_3$) MS: 158($M^+$, 6): m/e: 102(4), 85(60), 69(3), 57(100), 41(25), 29(21) $^1$H-NMR($CDCl_3$): 0.92(t, J=7, 3H); 1.13(d, J=7, 3H); 1.38(t, J=7, 3H); 1.45(m, 1H); 1.77(m, 1H); 3.14(m, 1H); 4.32(q, J=7, 2H) $^{13}$C-NMR($CDCl_3$): 3q: 11.4, 14.1, 14.6; 2t: 25.0, 62.2; 1d: 43.6; 2s: 162.1, 198.3

2. Synthesis of (−)-ethyl-(R)-3-methyl-2-oxopentanoate

The synthesis was carried out in three steps, according to the following scheme:

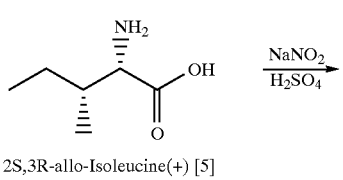

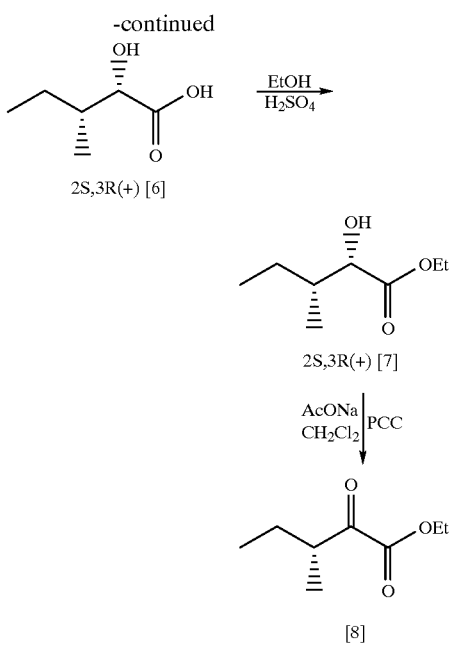

2.1. Synthesis of (+)-(2S, 3R)-2-hydroxy-3-methylpentanoic acid [6]

This compound was synthesised from (+)-L-allo isoleucine [5] ([α]$^D_{20}$=+37° (5% in 6M HCl)) as described in 1.1. (yield: 93%).

Analytical data: [α]$^D_{20}$=+18.7° (0.46% in CHCl$_3$) MS: 132(M$^+$, 0): m/e: 87(36), 76(100), 69(15), 57(28), 45(31), 29(19) $^1$H-NMR(CDCl$_3$): 0.89(d, J=7, 3H); 0.97(t, J=7, 3H); 1.38(m, 1H); 1.54(m, 1H); 1.80(m, 1H); 4.30(d, J$_1$=3) $^{13}$C-NMR(CDCl$_3$): 2q: 11.8, 13.1; 1t: 26.0; 2d: 38.3, 72.7; 1s: 178.9

2.2. Synthesis of (+)-ethyl-(2S, 3R)-2-hydroxy-3-methylpentanoate [7]

This compound has been synthesised from (+)-hydroxy acid [6] as described in 1.2. (yield: 66.4%).

Analytical data: [α]$^D_{20}$=+16.1° (0.91% in CHCl$_3$) MS: 160(M$^+$,1): m/e: 104(38), 87(90), 76(70), 69(37), 57(32), 45(100), 29(70) $^1$H-NMR(CDCl$_3$): 0.82(d, J=7, 3H); 0.96(t, J=7, 3H); 1.31(t, J=7, 3H); 1.34(m, 1H); 1.53(m, 1H); 1.81(m, 1H); 2.67(d, J=6, 1H, disappear by add. of D$_2$O); 4.18(dd, J$_1$=3, J$_2$=6, 1H, collapse to d, J=3 by add. of D$_2$O); 4.26(m, 2H) $^{13}$C-NMR(CDCl$_3$): 3q: 11.9, 13.1, 14.3; 2t: 26.0, 61.6; 2d: 38.5, 72.9; 1s: 175.4

2.3. Synthesis of (−)-ethyl-(R)-3-methyl-2-oxopentanoate [8]

This compound has been synthesised from (+)-hydroxy ester [7] as described in 1.3. (yield: 75%).

Analytical data: [α]$^D_{20}$=−36.1° (1.0% in CHCl$_3$) MS, $^1$H-NMR and $^{13}$C-NMR were superimposable with those obtained for the (+)-isomer (see 1.3.).

EXAMPLE 2

Perfuming Composition

A base perfuming composition having a floral-fern (fougère) character was prepared by admixing the following ingredients:

| Ingredients | Parts by weight |
|---|---|
| Benzyl acetate | 170 |
| 3,5,5-Trimethylcyclohexanyl acetate | 20 |
| Tricyclo(5.2.1.0.(2,6))dec-3-en-8-yl acetate | 20 |
| Citronellol | 40 |
| 10% Ethylvanilline* | 20 |
| Exolide ®[1] | 140 |
| Heliotropine | 40 |
| Iralia ®[2] | 100 |
| Lilial ®[3] | 100 |
| Linalol | 120 |
| Phenylethanol | 40 |
| Amyl Salicyclate | 40 |
| Benzyl Salicyclate | 120 |
| Total | 970 |

*in dipropylene glycol
[1] mixture of 1-oxacyclohexadecan-2-one and 1-oxa-(12,13)-cyclohexadecen-2-one; origin: Firmenich SA, Geneva, Switzerland
[2] mixture of methylionone isomers; origin: Firmenich SA, Geneva, Switzerland
[3] 3-(4-tert-butylphenyl)-2-methylpropanal; origin: Givandan-Roure SA, Vernier, Switzerland When 30 parts by weight of 3-methyl-2-oxo-ethylpentanoate or an isomer thereof were added to this base perfuming composition, the latter acquired a superb fruity connotation, with a very natural, light walnut undernote. In this manner, a very natural sparkling aspect was imparted to the composition, which was highly appreciated.

EXAMPLE 3

Perfuming Composition

A base perfuming composition having a rose-citrus character was prepared by admixing the following ingredients:

| Ingredients | Parts by weight |
|---|---|
| Dimethylbenzylcarbinyl acetate | 20 |
| Phenylethyl acetate | 30 |
| 10% Raspberry ketone | *5 |
| 10% **Cetalox ®[1] | 20 |
| Citronellol | 40 |
| Coumarine | 20 |
| Eugenol | 5 |
| Fructone ®[2] | 10 |
| Habanolide ®[3] | 120 |
| Hedione ®[4] | 100 |
| Iralia ®[5] | 60 |
| Lilial ®[6] | 35 |
| Lorysia ®[7] | 80 |
| Phenylhexanol | 140 |
| Hexyl Salicyclate | 60 |
| Tetrahydrolinalol | 120 |
| Verdox ®[8] | 30 |
| Vertofix Coeur ®[9] | 80 |
| Tamarine Base ®[10] | 35 |
| Total | 1000 |

*in dipropylene glycol
**in 2-(2-ethoxyethoxy)-1-ethanol; origin: Firmenich SA, Geneva, Switzerland
[1] 8,12-epoxy-13,14,15,16-tetranorlabdane; origin: Firmenich SA, Geneva, Switzerland
[2] 2-methyl-1,3-dioxolane-2-ethyl acetate; origin: International Flavors & Fragrances, USA
[3] pentadecenolide; origin: Firmenich SA, Geneva, Switzerland
[4] methyl dihydrojasmonate; origin: Firmenich SA, Geneva, Switzerland
[5] see example 1
[6] see example 1
[7] 4-(1,1-dimethylethyl)-1-cyclohexyl acetate; origin: Firmenich SA, Geneva, Switzerland
[8] 2-tert-butyl-1-cyclohexyl acetate; origin: International Flavors & Fragrances, USA
[9] origin: International Flavors and Fragrances, USA
[10] limonene based composition; origin: Firmenich SA, Geneva, Switzerland 30 Parts by weight of 3-methyl-2-oxo-ethyl-pentanoate or an isomer thereof were added to this floral base composition. A novel composition was thus obtained, having a fresher and more lifting connotation, thanks to the pleasant fruity note that the composition thus acquired.

What we claim is:

1. A method to produce, improve, enhance or modify the odor properties of a perfuming composition or a perfumed product, which method comprises adding 3-methyl-2-oxo-ethylpentanoate as a perfuming ingredient to said composition or product.

2. A perfuming composition or a perfumed product containing as active ingredient 3-methyl-2-oxo-ethyl-pentanoate.

3. Perfumed product according to claim 2, in the form of an after-shave lotion, a cosmetic preparation, a soap, a hair-care product, a bath or shower gel, a body or air deodorant, a detergent or a fabric softener, or a household product.

4. Perfumed product according to claim 2, in the form of a perfume or a cologne.

* * * * *